United States Patent [19]

Ahlstrom, Jr. et al.

[11] 4,452,067
[45] Jun. 5, 1984

[54] APPARATUS FOR ANALYSIS OF A VAPOR PHASE SAMPLE

[75] Inventors: Ross C. Ahlstrom, Jr., Lake Jackson; Craig E. Meppen, New Braunfels, both of Tex.

[73] Assignee: The Dow Chemical Company, Midland, Mich.

[21] Appl. No.: 412,699

[22] Filed: Aug. 30, 1982

[51] Int. Cl.³ .............................................. G01N 31/08
[52] U.S. Cl. .................................................... 73/23.1
[58] Field of Search ....................... 73/23.1; 55/67, 197, 55/386; 422/62, 89; 436/140, 161

[56] References Cited

U.S. PATENT DOCUMENTS

| | | | |
|---|---|---|---|
| 3,096,653 | 7/1963 | Martin et al. | 73/863.83 |
| 3,234,779 | 2/1966 | Dawson | 73/23.1 |
| 3,250,057 | 5/1966 | Clarke | 73/23.1 |
| 3,273,577 | 9/1966 | Moore | 137/13 |
| 3,357,158 | 12/1967 | Hollis | 55/67 |
| 3,385,101 | 5/1968 | Roof | 73/23.1 |
| 3,714,813 | 2/1973 | Martin | 73/23.1 |
| 3,865,562 | 2/1975 | Ayers et al. | 55/67 |
| 4,067,226 | 1/1978 | Ririe | 73/23.1 |
| 4,215,563 | 8/1980 | Clardy et al. | 73/23.1 |
| 4,272,481 | 6/1981 | Ahlstrom et al. | 422/62 |

*Primary Examiner*—Stephen A. Kreitman
*Attorney, Agent, or Firm*—Norman L. Sims

[57] ABSTRACT

The present analyzing apparatus provides a means for vapor phase analysis of process streams containing a non-condensable phase, and a condensable phase wherein the phases are variously comprised of hydrogen, water, oxides of carbon, aliphatic hydrocarbons and aromatic hydrocarbons. A sample is passed into a first separation means wherein the aromatic hydrocarbons are separated from the hydrogen, water, oxides of carbon and aliphatic hydrocarbon. The hydrogen, water oxides of carbon and aliphatic hydrocarbons are passed in a second separation means while the aromatic hydrocarbons are held in the first separation, and separated into the constituent elements and compounds and thereafter passed into a first detection means wherein the concentration of each constituent is determined. The aromatic hydrocarbons are passed from a first separation means to a third separation means where the aromatic hydrocarbons are separated into the constituent compounds. Thereafter the constituent compounds are passed into a second detection means where the concentration of each constituent is determined. The sample is kept in the vapor phase during the process.

13 Claims, 3 Drawing Figures

4,452,067

APPARATUS FOR ANALYSIS OF A VAPOR PHASE SAMPLE

BACKGROUND OF THE INVENTION

Broadly, the invention relates to analysis of a vapor phase sample. More specifically, the invention is directed to analysis of a vapor phase sample in which the sample, at ambient temperature and standard pressure, contains a mixture of condensed and non-condensed components. Such a sample when taken from a process stream or reactor would be in a vapor phase which contains materials which are condensable and non-condensable when cooled to normal room temperature at atmospheric pressure.

In some chemical processes the composition of the process mixture, at ambient temperature and standard pressure, includes a mixture of a non-condensed phase, an aqueous condensed phase, and a condensed organic phase. Ambient temperature means herein the temperature of the area outside of a process reactor or stream, also known as room temperature. An example of such a product is a mixture which contains water, hydrogen, oxides of carbon, aromatic hydrocarbons, and aliphatic hydrocarbons. It is very difficult to achieve reliable on-line analysis of such a mixture, particularly if the aromatic hydrocarbons are polymerizable materials.

The term condensable means herein that the gaseous phase sample condenses to the liquid phase sample at standard temperature and pressure. The term non-condensable means herein that the gaseous phase sample remains in the gaseous phase at standard temperature and pressure.

Heretofore, a vapor phase sample with condensable and non-condensable components including water, aromatic hydrocarbons, aliphatic hydrocarbons, hydrogen and oxides of carbon have been collected by cooling the sample to condense water, aromatic hydrocarbons and some aliphatic hydrocarbons. The water and organic phases formed separately and are analyzed separately. The non-condensable phase is difficult to analyze, because some of the water and aromatics become entrained in the non-condensable gas phase.

While chromatographic separations of the sample have been made in the above-described manner, no attempt has been made to analyze the total sample in the vapor state. In particular, no such method has been presented that is capable of separating and quantitatively detecting these components automatically. Prior art methods of separating complex mixtures make no provision for column switching with multiple detectors at temperatures of about 200° C. In particular, no provision is made for maintaining a uniform flow of carrier gas to the detector to minimize upsets during column switching and to optimize sensitivity.

The present invention provides an apparatus and method for analyzing a sample in the vapor phase. Further, this invention allows samples from a process reactor to be analyzed without manual handling of samples. This allows an accurate indication of the contents of the process stream which results in better control of the process.

DESCRIPTION OF THE DRAWINGS

The drawings are schematic illustrations of one embodiment of the vapor phase analyzing system of this invention. Each view illustrates the system as it appears during a specific operating sequence, as follows.

SUMMARY OF THE INVENTION

Figure 1:
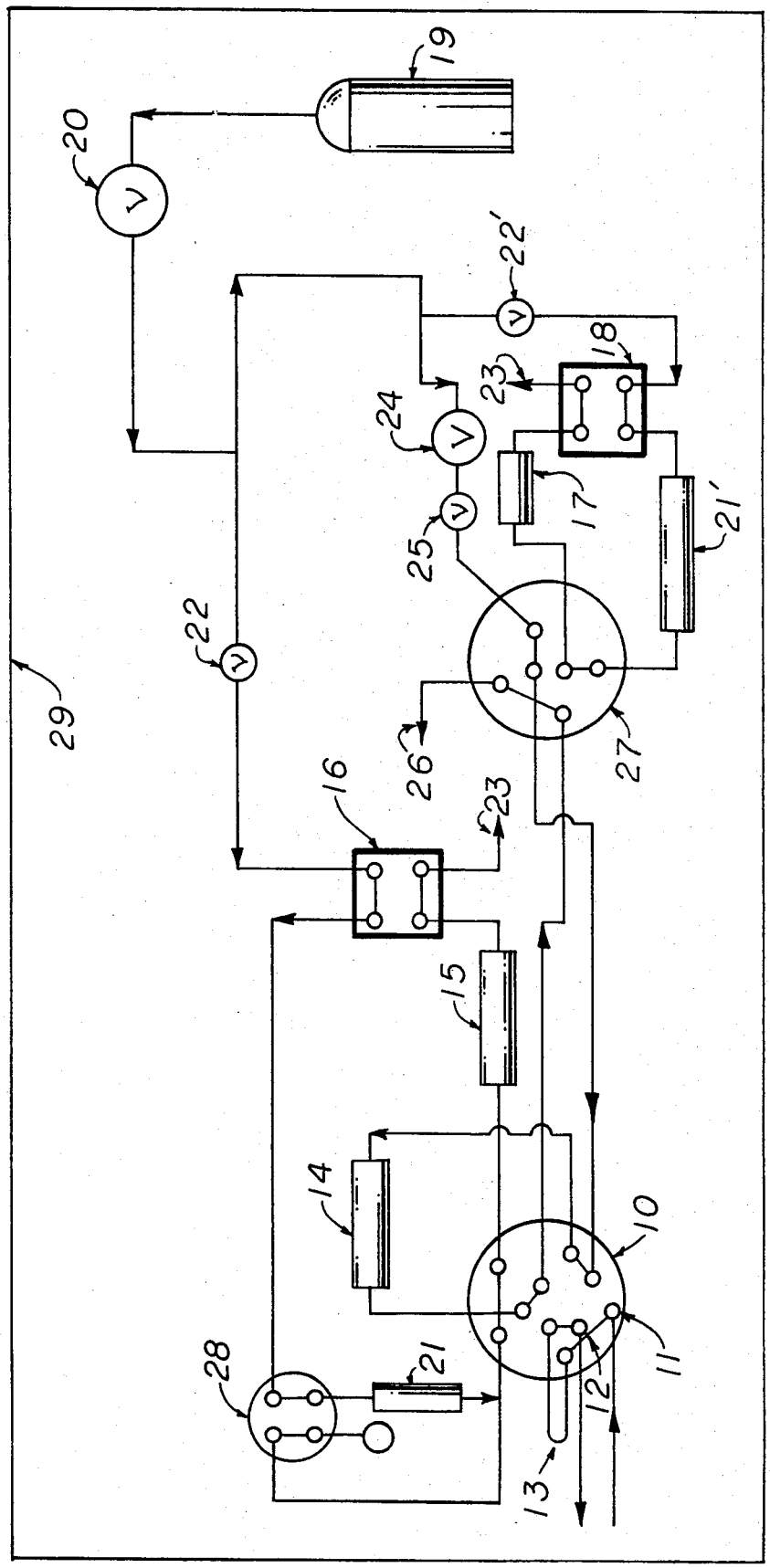
FIG. 1 shows the present analyzing system as it appears during the backflushing sequence.

The invention is a system for analyzing a vapor phase sample containing condensable and non-condensable components containing a mixture of hydrogen, oxides of carbon, water, aliphatic hydrocarbons and aromatic hydrocarbons. This invention includes a sample injection means, into which is connected a first separation means, which is adapted for separating the hydrogen, oxides of carbon, water and aliphatic hydrocarbons from the aromatic hydrocarbons. The first separation means is connected to a second separation means which is adapted for separating the hydrogen, oxides of carbon, water and aliphatic hydrocarbon portion of the sample into its constituent elements and compounds. The first separation means is further connected to a third separation means adapted for separating the aromatic hydrocarbon portion of the sample into its constituent compounds. Connected to the second separation means is a first detection means adapted for determining the concentration of each constituent element and compound of the hydrogen, oxides of carbon, water and aliphatic hydrocarbon portion of the sample. Connected to the third separation means is a second detection means adapted to determine the concentration of each constituent compound in the aromatic hydrocarbons portion of the sample. The apparatus further comprises a heater means associated with the analyzer system, for holding the analyzer system at a temperature sufficient to maintain all components of the sample in a vapor phase.

The invention further includes a method for analyzing the sample described above. A sample is passed from a process system into a sample injection means, which thereafter passes the sample into a first separation means. The hydrogen, oxides of carbon, water and aliphatic hydrocarbon portions of the sample are separated from the aromatic hydrocarbons in the first separation means. The hydrogen, oxides of carbon, water and aliphatic hydrocarbon portion of the sample is then passed from the first separation means to the second separation means wherein the hydrogen, oxides of carbon, water and aliphatic hydrocarbon portion of the sample is separated into its constituent compounds and elements, while the aromatic hydrocarbon portion of the sample is still in the first separation means. The constituent compounds and elements of the hydrogen, oxides of carbon, water and aliphatic portion of the sample are then passed from the second separation means through a first detection means which determines the concentration of each of the constituent elements and compounds. The aromatic hydrocarbon portion of the sample is passed from the first separation means to the third separation means wherein the aromatic hydrocarbon portion is separated into its constituent compounds. Thereafter the constituent compounds of the aromatic hydrocarbon portion are passed through a second detection means to determine their concentration. The sample is heated to a temperature sufficient to maintain the sample in a vapor phase during each step of the method defined herein.

DESCRIPTION OF A PREFERRED EMBODIMENT

Referring to FIG. 1, the numeral 10 refers to a port valve having 10 ports. Connected into the port valve 10 is the sample inlet 11, into which a sample stream of the system to be analyzed is passed. The sample inlet is connected to a sample delivery system or directly to a process reactor from which the sample to be analyzed is taken. Also connected to the valve 10 is the sample outlet 12, which is adapted for carrying the portion of the sample stream which is not introduced into the analyzer apparatus for analysis, away from the apparatus. Also connected into valve 10 is a sample loop 13, which is adapted for accepting the sample stream from the sample inlet 11 and either passing the sample stream out of the analyzer through the sample outlet 12, or introducing the portion of the sample in the sample loop into the analyzer, depending upon how valve 10 is set. Also connected to the sample loop 13 by the port valve 10 is the first separation means 14, which is adapted for separating the aromatic hydrocarbons in the sample, from the hydrogen, water, oxides of carbon and aliphatic hydrocarbons in the sample.

This first separation means is preferably a chromatographic column. Connected to column 14 is a second separation means 15, which is adapted for separating the portion of the sample which includes hydrogen, water, oxides of carbon and aliphatic hydrocarbons into its constituent elements and compounds. The second separation means is preferably a chromatographic column. Connected to column 15, is a first detection means 16, which is adapted for determining the concentration of each of the constituent elements and compounds contained in the portion of the sample which includes hydrogen, water, oxides of carbon and aliphatic hydrocarbons. This first detection means includes any apparatus which is adapted for the purpose described above, and is preferably a thermal conductivity detector.

Also connected to column 14 is a third separation means 17, which is adapted for separating the aromatic hydrocarbon portion of the sample into its constituent elements. This third separation means is preferably a chromatographic column. Both column 15 and column 17 are connected to column 14, and the first valve 10 functions to direct the flow from column 14 to either column 15 or column 17. Connected to column 17 is a second detection means 18, which is adapted for determining the concentration of each of the constituent compounds of the aromatic hydrocarbon portion of the sample. The second detection means can be any apparatus or method adapted for the purpose described above such as a thermal conductivity detector.

The present analyzing system further includes a source of carrier gas 19. A means of regulating the pressure in the analyzing apparatus is provided by a valve 20, which is located between the source of the carrier gas and the remainder of the apparatus. Connected into each of the two detection means is a means for balancing the flow of carrier gas to both detection means, so as to minimize any tendency for the detection means to drift. These flow balancing means of balancing flow are preferably chromatographic columns 21 and 21', which are located between the source of carrier gas and each of the detection means.

Valve 10 is further adapted for switching the flow from column 14 between column 15 and column 17. This switching can cause interruption in flow through column 15 and column 17 and the first and second detection means which are respectively connected to the columns. This interruption of flow can cause fluctuation in the reference flow in the detection means, which can cause error in the analytical data generated. The flow balancing means 21 and 21' serves to minimize this upset, in conjunction with valve 28.

Where the means of balancing flow are chromatographic columns, they are packed with material through which the carrier gas flows in the same manner as the carrier gas flows through the separation means the flow balancing means is connected into. When this analyzer is used to continuously sample one or more process streams, numerous switchings occur and these means of balancing flow prevent such switching from causing error in the analytical data generated.

Located between the source of carrier gas and each means of balancing flow are two valves 22 and 22' for regulating the flow of carrier gas to each of the detection means. A sample discharge means 23 is also connected into each detector means. The discharge means allows the sample to leave the analyzer.

This invention further includes a means of backflushing the analyzing apparatus to remove any traces of material previously sampled. In the backflushing sequence, as illustrated in FIG. 1, the source of carrier gas is also used as a source of material for backflushing the system. Connected into the source of carrier gas and located between the source of carrier gas and column 14 is a backflush valve 24. This valve is adapted for regulating the flow of carrier gas through the analyzer during backflush. Connected into the backflush valve is a flow regulation valve 25 adapted for adjusting the flow of carrier gas during backflush. This embodiment further includes a venting means 26, adapted for carrying the carrier gas and any backflushed material out of the analyzing apparatus.

The present analyzing system further includes a means adapted for heating the apparatus to keep the sample in the vapor phase. The heating means can be selected from several suitable embodiments. The entire apparatus can be enclosed in a heating means, for example, as indicated by numeral 29. Alternatively, each separation means can be individually heated, an airbath oven can be used in either embodiment. If necessary, the sample delivery system can also be heated to keep the sample in the vapor phase. Hot oil, steam and electric heat are suitable heating means for this purpose.

OPERATION

In a typical operation, the present analyzer system can be connected into any number of reactors or other types of chemical process apparatus. This feature of the invention permits continuous vapor phase analysis of an indefinite number of process streams in a single operation. In actual practice, the number of process streams which can be tied into an analyzing apparatus will depend on the specific requirements of the chemical process which is being sampled.

Figure 2:
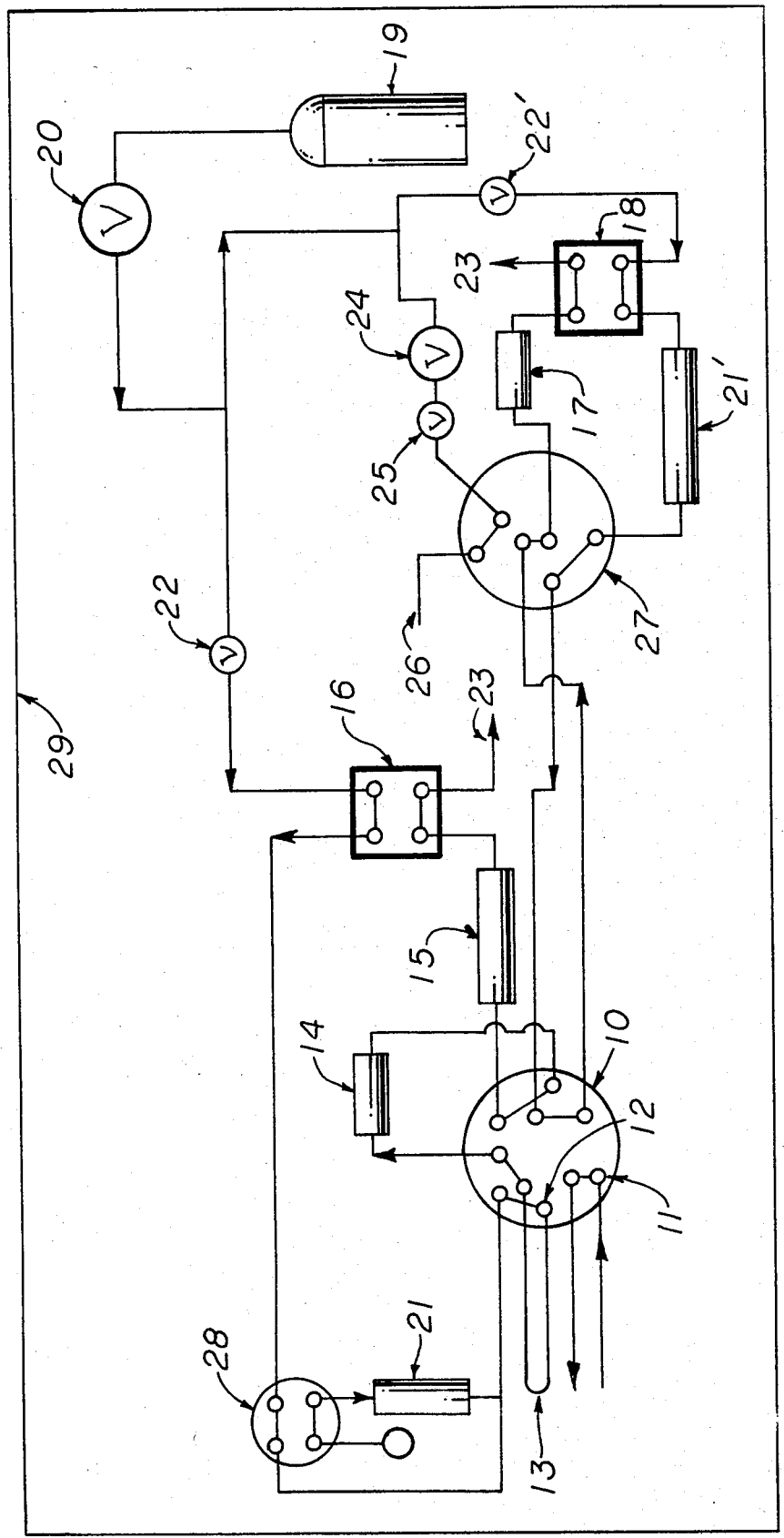
FIG. 2 shows the system as it appears during the sample injection sequence.

Referring to the Figures, the analyzer system has three different operating sequences which are used during the analysis of a sample. The first sequence is the backflush position (see FIG. 1), the second is the sample inject position (see FIG. 2), and the third is the component separation position (see FIG. 3). The various positions are achieved by the use of valve 10 having 10 ports, valve 27 having 6 ports, and valve 28 having 4 ports. Changing of the valves to achieve the desired positions can be done manually or through the use of a timing sequence module. The timing sequence module can also automatically control the backflush valve. The use of a timing sequence module can aid in the continuous sampling of one or more process streams.

This analyzer can be connected into an automatic process control system wherein the chemical composition of a process stream or streams can be continuously fed into such process control system. Included in such process control systems would be computers adapted for controlling a process.

In a representative operation, the process stream to be sampled may contain hydrogen and oxides of carbon, as a non-condensable phase; water and certain aromatic hydrocarbons which dissolve therein, as a condensable aqueous phase; and certain aromatic and aliphatic hydrocarbons, as the condensable organic phase. To start the operation the analyzer system is first set at the backflush position. While in this position, the analyzer is backflushed by carrier gas to remove the previous sample. At the same time, the sample stream enters the sample inlet 11 and continuously flows through the sample loop 13, exiting at the sample outlet 12.

Thereafter valves 10, 27 and 28 are adjusted to the sample inject position and the portion of the sample then in the sample loop 13 is passed into column 14. In column 14, the hydrogen, oxides of carbon, water and aliphatic hydrocarbons in the sample are separated from the aromatic hydrocarbons in the sample. The portion of the sample containing water, hydrogen, oxides of carbon and aliphatic hydrocarbons is then passed into column 15, while the aromatic hydrocarbons from the sample are held in column 14. Where the first separation means 14 is a chromatographic column, the hydrogen, oxides of carbon, water and aliphatic hydrocarbons elute from the column and are passed into the second separation means before the aromatic hydrocarbons elute from the column.

Figure 3:
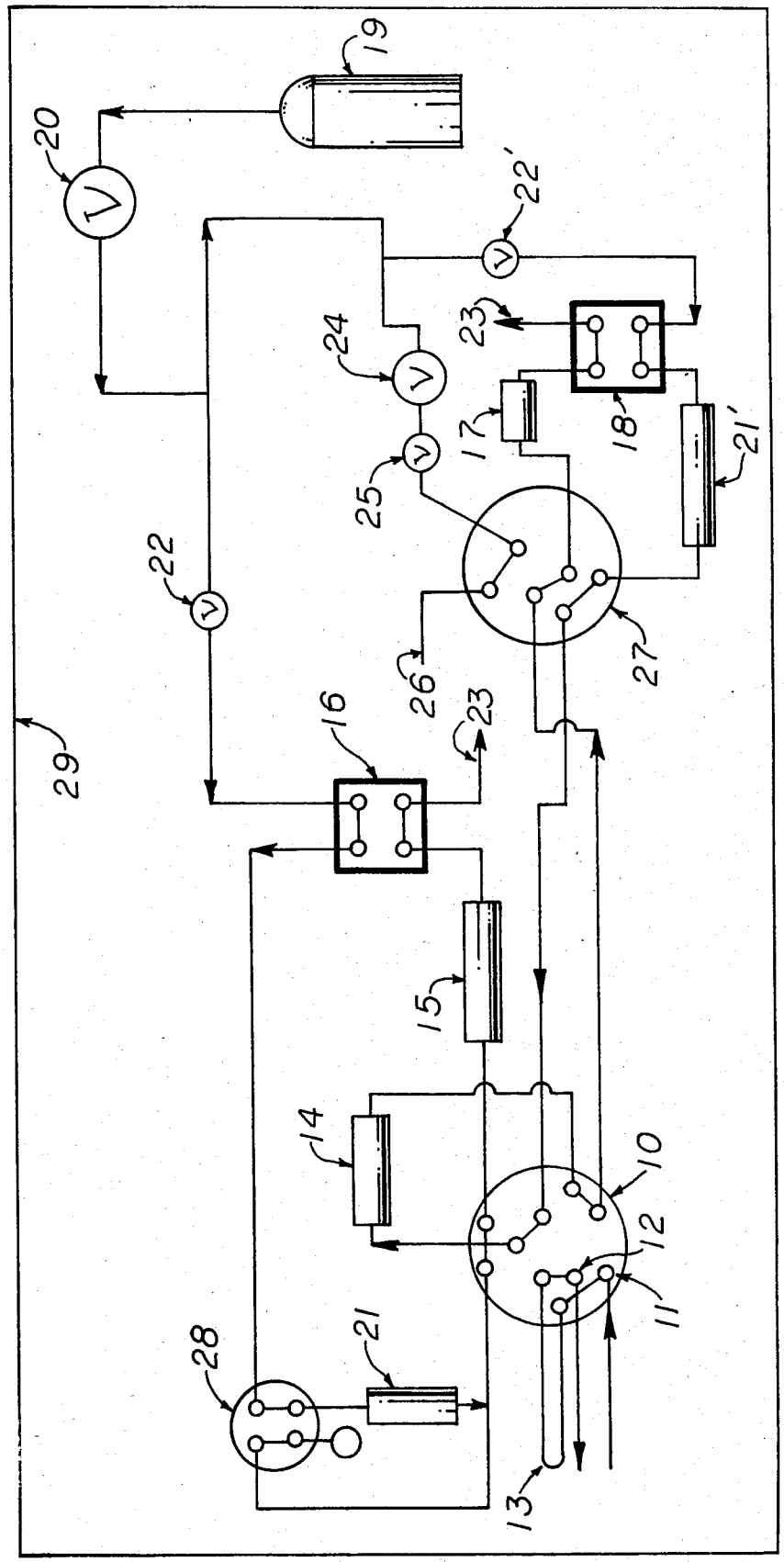
FIG. 3 shows the system as it appears during the component separation sequence.

After the hydrogen, oxides of carbon, water and aliphatic hydrocarbons have passed from column 14, and while the aromatic hydrocarbons are still in column 14, valves 10 and 28 are changed to the component separation position setting, thereby connecting column 14 with column 17 as shown in FIG. 3. The aromatic hydrocarbons are then passed from column 14 to column 17. The hydrogen, oxides of carbon, water and aliphatic hydrocarbons are then separated into their constituent elements and compounds in column 15. Following this, the constituents are passed to the first detection means 16, wherein each of their concentrations are determined. The constituent elements and compounds of the hydrogen, oxides of carbon, water and aliphatic hydrocarbons are then removed from the apparatus. Simultaneously, the aromatic hydrocarbons are separated into their constituent compounds in column 17 and then passed into the second detection means 18, in which the concentration of each of the constituent compounds is determined. Thereafter, the constituent compounds are removed from the analyzer through the discharge means 23.

After the desired sample has been passed from column 14 to column 17, valve 28 is switched back to the backflush position, to ready the analyzer apparatus for the next sample.

In the operation described above, the carrier gas flows through the two flow balancing means 21 and 21' prior to going through columns 14, 15 and 17, and the two detection means 16 and 18. This minimizes drift in the detectors. This flow balancing function is important where a process system is being continuously analyzed. Without it, the detectors would tend to drift.

The actual temperature and pressure of the system during analysis will vary according to the composition of the sample to be analyzed. Where the sample includes a non-condensable phase, a condensable organic phase and a condensable water phase, the temperature and pressure must be such as to keep all three phases in the vapor state. Only in the vapor phase can all of the constituent elements and compounds be separated one from another and their concentrations accurately determined.

In the practice of this invention, as described herein, the analyzing system is particularly adapted for analyzing process streams in which the components are made up of a non-condensable phase, a condensable aqueous phase, and a condensable organic liquid phase. The stream from a styrene process is typical of one which contains components which partially condense to these phases at atmospheric pressure and normal room temperature.

This apparatus and method is an improvement over the prior art because it allows quick and accurate analysis of a process stream in the vapor phase. The prior art methods of analysis require separation and separate analysis of a non-condensable phase, an aqueous phase and an organic phase wherein the latter two are condensed when analyzed. This separation and separate analysis is cumbersome and slow. Further accurate analysis becomes difficult because the analysis is done on samples in two different phases. The apparatus and method described herein avoid these problems by analyzing the sample in the vapor phase without the necessity of separating the sample into a non-condensable phase, a condensable organic phase and a condensable aqueous phase.

What is claimed is:

1. A system for analyzing a vapor phase sample containing non-condensable and condensable components, containing a mixture of hydrogen, oxides of carbon, water, aliphatic hydrocarbons and aromatic hydrocarbons, the system comprising:
   (a) a sample injection means;
   (b) a first separation means which connects into the sample injection means, and the first separation means is adapted for separating the hydrogen, oxides of carbon, water and aliphatic hydrocarbons from the aromatic hydrocarbons;
   (c) a second separation means which is connected into the first separation means, and the second separation means is adapted for separating the hydrogen, oxides of carbon, water and aliphatic hydrocarbons into the constituent elements and compounds;
   (d) a first detection means which is connected into the second separating means, and the first detection means is adapted for determining the concentration of the constituent elements and compounds in the hydrogen, oxides of carbon, water and aliphatic hydrocarbons;
   (e) a third separation means which is connected into the first separation means, and the third separation means is adapted for separating the aromatic hydrocarbons into the constituent compounds;

(f) a second detection means which is connected into the third separation means, and the second detection means is adapted for determining the concentration of each constituent compound of the aromatic hydrocarbon; and (g) a heater means associated with the analyzer system, for holding the analyzer system at a temperature sufficient to maintain all components of the sample in a vapor phase.

2. The system of claim 1 wherein the condensable phase comprises an aqueous phase and an organic phase.

3. The system of claim 1 wherein the first separation means is a chromatographic column.

4. The system of claim 1 wherein the second separation means is a chromatographic column.

5. The system of claim 1 wherein the third separation means is a chromatographic column.

6. The system of claim 1 wherein the first detection means is a thermal conductivity detector.

7. The system of claim 1 wherein the second detection means is a thermal conductivity detector.

8. The system of claim 1 which further includes a means for balancing the flow to the first detection means, which is connected into the first detection means.

9. The system of claim 8 wherein the flow-balancing means is a chromatographic column.

10. The system of claim 1 which further includes a means for balancing the flow to the second detection means, which is connected into the second detection means.

11. The system of claim 10 wherein the flow-balancing means is a chromatographic column.

12. The system of claim 1 which further includes a timing sequence module to regulate the timing of the flow of the sample through the analyzer.

13. A method for analyzing a vapor phase sample containing non-condensable and condensable components, comprising hydrogen, oxides of carbon, water, aliphatic hydrocarbons and aromatic hydrocarbons, the method comprising the steps of:

(a) passing the sample from a process system into a sample injection means;

(b) injecting the sample from the sample injection means into a first separation means;

(c) separating the hydrogen, oxides of carbon, water and aliphatic hydrocarbons from the aromatic hydrocarbons in the first separation means;

(d) passing the hydrogen, oxides of carbon, water and aliphatic hydrocarbons from the first separation means into a second separation means, while holding the aromatic hydrocarbons in the first separation means;

(e) separating the hydrogen, oxides of carbon, water and aliphatic hydrocarbons into constituent elements and compounds in the second separation means;

(f) passing the constituent elements and compounds of hydrogen, oxides of carbon, water and aliphatic hydrocarbons from the second separation means through a first detection means, to determine the concentration of each of the elements and compounds;

(g) passing the aromatic hydrocarbons from the first separation means into a third separation means;

(h) separating the aromatic hydrocarbons into the constituent compounds in the third separation means;

(i) passing the constituent compounds of the aromatic hydrocarbons through a second detection means to determine the concentration of each constituent compound in the organic phase; and (j) heating the sample to a temperature sufficient to maintain said sample in a vapor phase during each step of the method defined herein.

* * * * *